United States Patent [19]

Yabe

[11] Patent Number: 4,832,003
[45] Date of Patent: May 23, 1989

[54] ELECTRONIC ENDOSCOPE TIP

[75] Inventor: Hisao Yabe, Tokyo, Japan

[73] Assignee: Olympus Optical Co., Ltd., Tokyo, Japan

[21] Appl. No.: 95,202

[22] Filed: Sep. 11, 1987

[30] Foreign Application Priority Data

Sep. 12, 1986 [JP] Japan .................................. 61-216817
Mar. 12, 1987 [JP] Japan .................................. 62-057281

[51] Int. Cl.⁴ .............................................. A61B 1/06
[52] U.S. Cl. ......................................... 128/6; 358/98
[58] Field of Search ............................... 128/6; 358/98

[56] References Cited

U.S. PATENT DOCUMENTS 4,573,450  3/1986  Arakawa .
4,692,608  9/1987  Cooper et al. ........................... 128/6
4,697,210  9/1987  Toyota et al. ........................... 128/6
4,745,470  5/1988  Yabe

FOREIGN PATENT DOCUMENTS 60-241011  11/1985  Japan .
60-184017  12/1985  Japan .

Primary Examiner—Leo P. Picard
Attorney, Agent, or Firm—Armstrong, Nikaido, Marmelstein, Kubovcik & Murray

[57] ABSTRACT

A solid state imaging device chip is contained in a tip of an insertable part and has its imaging surface arranged in parallel with the axis of the insertable part. The solid state imaging device chip is fitted to one surface side of a base member. A circuit substrate fitted with an electronic part is connected to this one surface side of the base member in order to make the tip small in diameter.

33 Claims, 7 Drawing Sheets

ELECTRONIC ENDOSCOPE TIP

BACKGROUND OF THE INVENTION

Field of the Invention and Related Art Statement

This invention relates to an electronic endoscope tip provided with a solid state imaging device.

Recently, instead of an optical endoscope for observing a body interior image by using fibers, an electronic endoscope provided with such solid state imaging device as a CCD (charge coupled device) in the tip of an insertable part has come to be developed. In such endoscope, it is desired to make the tip small in the diameter from the necessity of reducing the pain of the patient when it is inserted.

The above mentioned solid state imaging device is generally rectangular or square and therefore will occupy a comparatively large space in case it is contained in the tip of an insertable part. Therefore, for example, in the publication of Japanese utility model laid open No. 184017/1985, it is suggested that the optical axis of an objective optical system is deflected by such optical device as a prism and is led to a solid state imaging device provided in parallel with the lengthwise direction of an insertable part to make the tip of the insertable part small in the diameter.

However, in the above mentioned prior art example, a substrate for mounting an electronic part is provided on the side reverse to such optical device as a prism so as to be overlapped with the solid state imaging device and therefore the thickness of the part in which the prism, solid state imaging device and substrate are arranged will become so large that there has been a defect that the tip can not be made small enough in the diameter.

Also, in Japanese patent laid open No. 241011/1985 or U.S. Pat. No. 4,573,450, it is suggested that the optical axis of an objective optical system is deflected substantially at right angles by an optical device and a solid state imaging device is arranged substantially in parallel with the inserting axis of an endoscope to make the tip small in the diameter.

These two prior art examples have the same defect as of the first prior art example.

Now, in the tip of an endoscope, not only a solid state imaging device chip but also a clock generating integrated circuit for driving the solid state imaging device and an amplifier for amplifying the image output from the solid state imaging device must be incorporated. In such case, if the solid state imaging device chip is once packaged and is connected with a substrate fitted with the other electronic part, a space for the connecting part will have to be provided, the endoscope tip will become thick and the rigid tip part will become long.

In the above mentioned three prior art examples, if the electronic part is fitted, the outside diameter of the rigid tip will have to be made larger, a great pain will be forced to the patient when the tip is inserted into the body cavity and the insertable cases will be restricted.

OBJECTS AND SUMMARY OF THE INVENTION

An object of the present invention is to provide an electronic endoscope wherein the insertable part tip containing a solid state imaging device can be made small in the diameter.

Another object of the present invention is to provide an electronic endoscope wherein circuit parts contained within the tip are easy to fit.

In the electronic endoscope of the present invention, the optical axis of an objective optical system is deflected in the direction substantially at right angles by an optical device, an optical image is led to a solid state imaging device arranged so that its imaging surface may be substantially parallel with the axis of the insertable part and a circuit substrate fitted with an electronic part is provided on one surface side fitted with the solid state imaging device in a base member so that the tip may be made small in the diameter and further the circuit substrate and the like may be easily fitted.

BRIEF DESCRIPTION OF THE DRAWINGS

FIGS. 1 to 4 relate to the first embodiment of the present invention.

Figure 4:
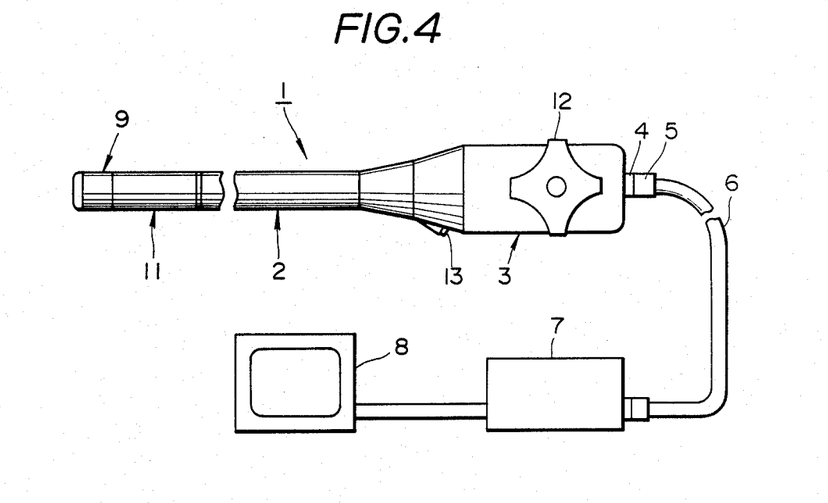
FIG. 4 is a side view showing an entire electronic endoscope provided with the first embodiment of the present invention.

DETAILED DESCRIPTION OF PREFERRED EMBODIMENTS:

As shown in FIG. 4, in an electronic endoscope 1 provided with the first embodiment, an operating part 3 larger in the diameter is provided as connected to the rear end of an elongated and, for example, flexible insertable part 2. A connector receiver 4 is provided at the rear end of the above mentioned operating part 3 so that the above mentioned operating part 3 may be connected with a control device 7 containing a light source device and image signal processing circuit through a cable 6 having a connector 5 to be fitted to this connector receiver 4. Further, a color monitor 8 as a displaying means is to be connected to the above mentioned control device 7. On the distal side of the above mentioned insertable part 2, a tip 9 and a curvable part 11 adjacent to this tip 9 and curvable rearward are provided in turn. By rotating and operating a curving operation knob 12 provided on the above mentioned operating part 3, the above mentioned curvable part 11 can be curved in the horizontal direction or vertical direction. An inserting port 13 communicating with a treating tool channel provided within the above mentioned insertable part 2 is provided in the above mentioned operating part 3.

Figure 1:
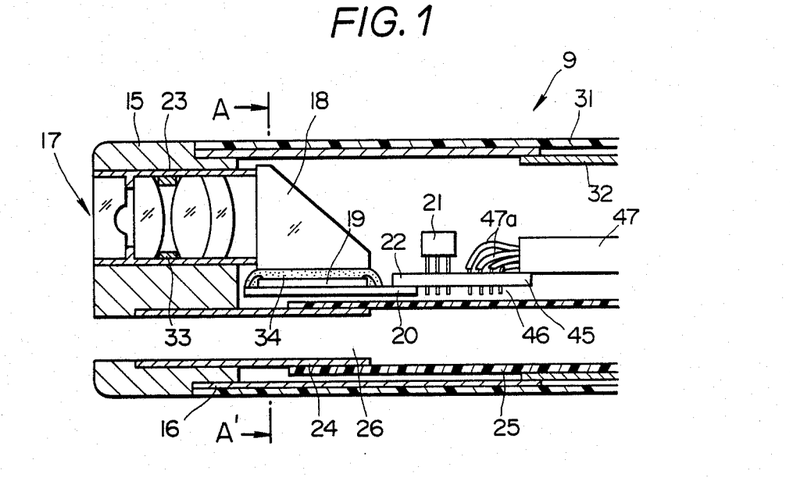
FIG. 1 is a sectioned view showing the structure of a tip of the first embodiment.

The above mentioned tip 9 is formed as shown in FIG. 1.

That is to say, in the tip 9, a tip pipe 16 is secured to the rear side of a columnar tip forming member 15 made of such rigid member as a metal to form a tip containing part containing an objective system 17, prism 18, CCD chip 19 as a solid state imaging device, CCD base 20 packaging the CCD chip 19 and substrate 22 connected to this CCD base 20 and fitted with an electronic part 21.

A through hole is formed to be eccentric, for example, to the upper side from the center in the above mentioned tip forming member 15 to fit the objective system 17 through a lens frame 23. A mouthpiece 24 is fitted in a through hole below this lens frame 23. A tube 25 made of a synthetic resin or rubber is fitted at the front end to the rear end of this mouthpiece 24 to form a treating tool channel 26.

Figure 2:
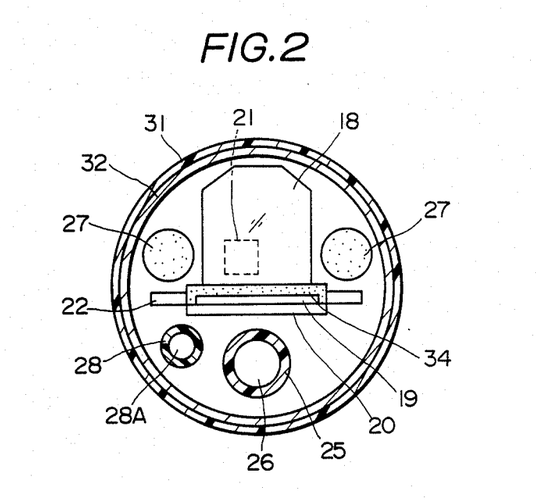
FIG. 2 is a schematic sectioned view on line A—A' in FIG. 1.

In the above mentioned tip forming member 15, light guides 27 arranged as shown in FIG. 2 by providing through holes on both sides (vertically above and below the paper surface in FIG. 1) of the lens frame 23, for example, in FIG. 1 are fixed at the front ends.

Also, as shown in FIG. 2, a tube 28 forming an air and water feeding channel 28A is inserted adjacently to the treating tool channel 26.

The above mentioned tip pipe 16 is coated on the outer periphery with a jacket cover 31. An articulating frame 32 forming the curvable part 11 is pivoted at the rear end of this tip pipe 16.

A spacer 33 is fitted to the above mentioned lens frame 23 to hold the respective lenses forming the objective system 17 at a predetermined spacing.

A prism 18 reflecting the beam incident in the optical axial direction of this objective system 17 to be deflected in the direction at right angles is arranged in the inner part of this objective system 17. The beam reflected in the direction at right angles by the sloped surface of this prism 18 is incident upon the imaging surface of the CCD chip 19 sealed with a light transmissive resin 34 on the periphery of the imaging surface so that the imaging surface may be parallel.

Figure 3:
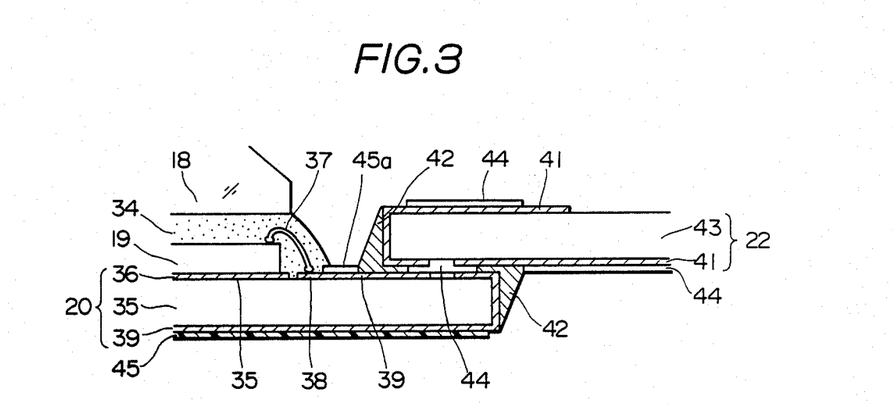
FIG. 3 is a sectioned view showing as magnified the connecting part of a base with a substrate in FIG. 1.

As shown in FIG. 3, the above mentioned CCD chip 19 is die-bonded to a die-bonding pad 36 provided on the upper surface of a base member 35 forming a CCD base on the back surface. This die-bonding pad 36 is gold-plated. The chip side bonding pad provided on the peripheral side of the imaging surface is connected to the base side bonding pad 38 on the upper surface of the CCD base member 35 by a bonding wire 37.

The above mentioned base side bonding pad 38 is extended to the end part (rear end side of the tip 9) of the base member 35 by the gold-plated printed pattern 39 and is connected by soldering 42 with the printed pattern 41 of the substrate 22 fitted with the electronic part. This substrate 22 consists of a base member 43 and a printed pattern 41 and protective resist 44 formed on this base member 43. This substrate 22 is mounted on the front end side on the upper surface at the rear end of the base 20. In such case, the respective base side printed patterns 39 and respective substrate side printed patterns 41 are fitted to the substrate 22 by soldering as substantially overlapped with each other. Many of both printed patterns 39 and 41 are formed as separated little by little in the direction vertical to the paper surface in FIG. 3. The printed pattern 39 part formed on the back surface of the base member 35 and extended to the upper surface side through the side surface at the rear end is electrically connected by soldering 42 with the printed pattern 41 on the back surface side of the substrate 22 and, by this soldering, the substrate 22 is mechanically fitted to the CCD base 20. The resist (represented by the reference numeral 45a) covering the printed pattern 39 part conducting to the above mentioned base side bonding pad 38 and adjacent to this pad 38 protects the light transmissive resin 34 from the heat in the case of soldering 42.

The base member 35 is coated on both surfaces except the parts to be soldered with a resist 45 and the substrate 22 side is also coated with a resist 44. the part in which the printed patterns 41 are interrupted between the electrically connecting and mechanically securing solderings 42 is covered with the resist 44 so that the insulation may not be insufficient in the case of soldering.

The substrate 22 fitted to the front surface side of the CCD base 20 (the plate surface side fitted with the CCD chip 19, prism 18 surface side or surface side upon which the imaging beam is incident) on the rear end side (the proximal side end) of the above mentioned CCD base 20 is fitted with the electronic part 21 as shown in FIG. 1. This electronic part 21 is a driving circuit for operating the CCD chip 19 or a circuit element or integrated circuit element forming a preamplifier or the like amplifying with a low noise index the feeble image signal in the case of converting the optical image on the imaging surface to an electric signal, is electrically connected with a circuit element or CCD chip 19 through the printed pattern 41 formed on the substrate 22 or the CCD base side printed pattern 39 or is electrically connected with the signal cable connecting part 46 by the through hole land or the like on the rear end side of this substrate 22. Respective signal lines 47a forming a signal cable 47 are connected as by soldering to this signal connecting part 46.

According to the electronic endoscope 1 of the thus formed first embodiment, the substrate 22 to be fitted with the electronic part 21 or the like is provided on the CCD base 20 fitted with the CCD chip 19 so that its front end side may be secured on the front surface side instead of the back surface side on the side reverse to the surface on which the CCD chip 19 is fitted. Therefore, the necessity of making the tip 9 large in the diameter by the thickness of this substrate 22 or by the thickness of the electronic part to be fitted to this substrate 22 is dissolved. That is to say, the tip 9 can be made small in diameter.

Also, the electronic part 21 and the respective signal lines 47a project on the surface side through the through holes of the substrate 22 but the projecting amount is made less than the thickness of the CCD base 20 and therefore it is dissolved that the tip 9 must be made larger in the diameter by the projecting amount.

When the CCD base 20, to be fitted with the CCD chip 19 and the substrate 22, to be fitted with the electronic part 21, are made separate from each other, the CCD chip 19 and its CCD base 20 can be used in common for various functions of the electronic endoscope.

Figure 5:
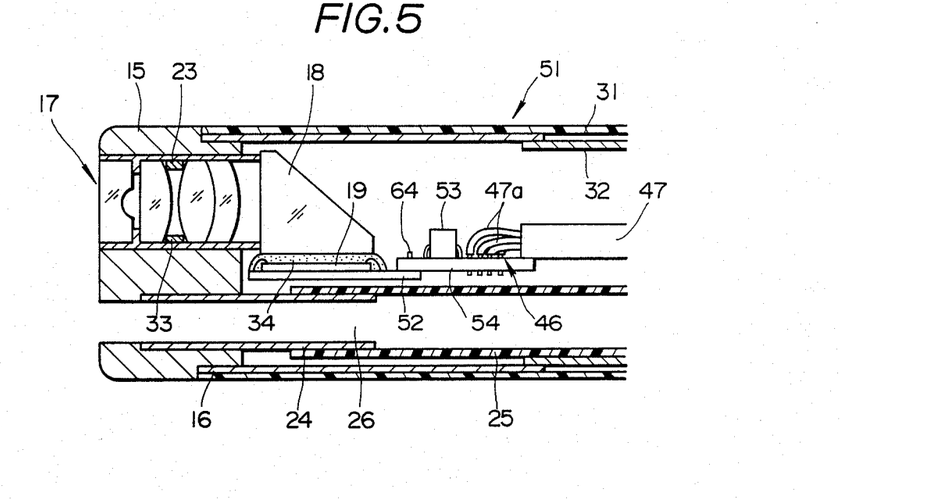
FIG. 5 is a sectioned view showing the structure of a tip of the second embodiment of the present invention.
Figure 6:
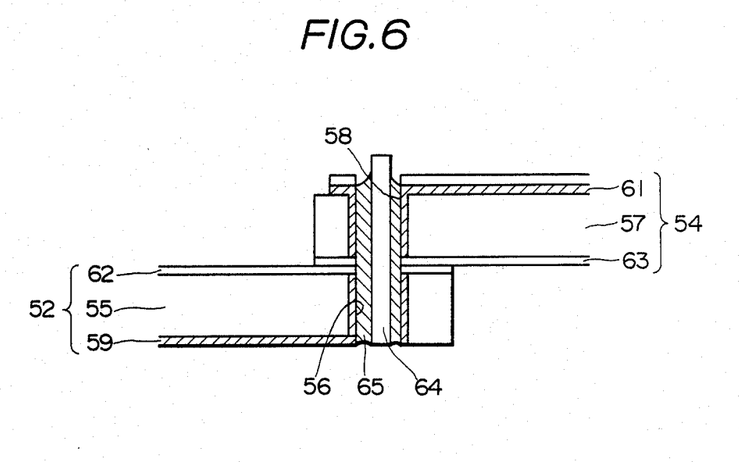
FIG. 6 is a sectioned view showing as magnified the connecting part of a base with a substrate in the second embodiment of the present invention.

FIG. 5 shows a tip 51 in the second embodiment of the present invention. FIG. 6 shows as magnified the structure of the connecting part of a substrate 54 to be fitted with a CCD base 52 and integrated circuit 53.

This second embodiment is substantially the same as is shown in FIG. 1 in the structure of the tip 51 but is different as shown in FIG. 6 in the structure of the connecting part of the CCD base 52 with the substrate 54.

That is to say, a plurality of landless through holes 56 are provided at minute spacings in the direction vertical to the paper surface in FIG. 6 near the rear end of a base member 55 forming the CCD base 52. Also, landless through holes 58 are formed at the front end of the base member 57 forming the substrate 54 at the same pitch as the spacings. The above mentioned CCD base 52 side landless through holes 56 conduct with the gold-plated printed wiring 59 formed on the back surface, for example, of the base member 55 and also the substrate 54 side landless through holes 58 conduct with a printed wiring 61, for example, on the upper surface of the base member 57. Resists 62 and 63 are provided respectively on the front surface of the base member 55 and the back surface of the base member 57.

A metal pin 64 high in the plateability is inserted into both landless through holes 56 and 58 as connected with each other. Both through holes 56 and 58 are electrically conducted with each other by soldering 65 and the substrate 54 is mechanically fixed to the base 52. The others are the same as in the above mentioned first embodiment. The same reference numerals are attached to the same corresponding members.

According to this second embodiment, when the landless through holes 56 and 58 of a diameter, for example, of about 0.4 mm. are used, the spacing between the adjacent landless through holes 56 (or 58) can be set to be about 0.6 mm. and therefore the connecting parts can be realized at a density higher than in the case of through holes having lands. Therefore, in case the base side and substrate side must be connected with each other with many through holes, the connecting part must be made wider in the prior art example but can be made smaller in the second embodiment and the tip 51 can be made small in the diameter.

Figure 7:
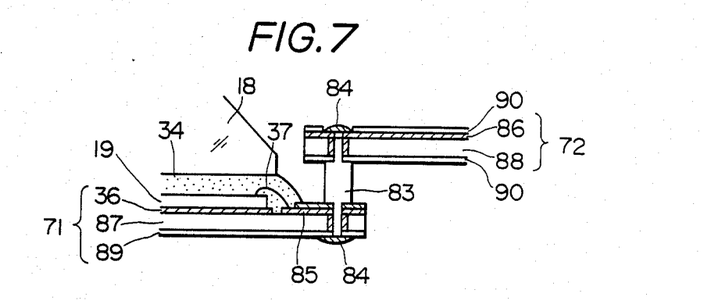
FIG. 7 is a sectioned view showing the connecting part of a base with a substrate in the third embodiment of the present invention.

As in the connecting part of a base 71 with a substrate 72 in the third embodiment of the present invention shown in FIG. 7, a metallic stay 83 is fitted in the small diameter parts at both ends into the respective through holes 56 and 58 and is fixed with solders 84 so that a base side printed wiring 85 and a substrate side printed wiring 86 may be electrically connected with each other and the substrate 72 may be mechanically fixed to the base 71. The back surfaces of the base member 87 and base member 88 and the front surfaces of the printed wirings 85 and 86 are coated respectively with resists 89 and 90.

The others are of the same structure as of the above mentioned first embodiment.

Figure 8:
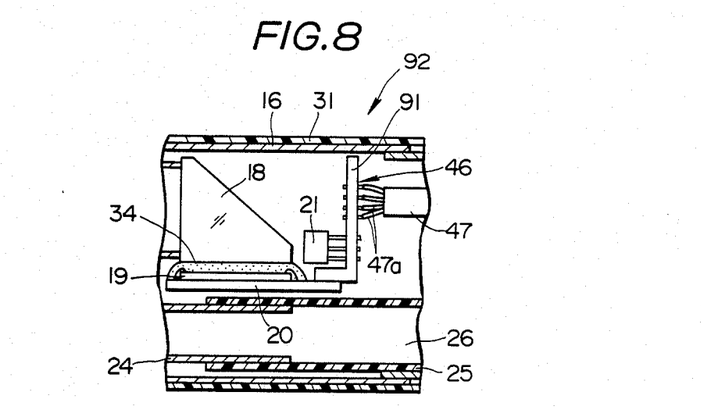
FIG. 8 is a sectioned view showing a tip of the fourth embodiment of the present invention.

As in the connecting part of the base 20 with a substrate 91 in the fourth embodiment shown in FIG. 8, for example, in the substrate 22 shown in FIG. 1, the substrate 91 can be bent upward at right angles to reduce the length of a rigid tip 92. In this case, the respective signal lines 47a of the signal cable 47 are connected to the signal cable connecting part 46, for example, by the through holes from the rear of the bent substrate 91.

Figure 9:
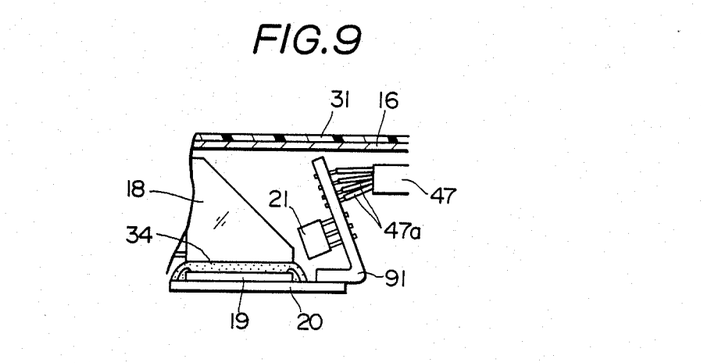
FIG. 9 is a sectioned view showing an essential part of a tip in the fifth embodiment of the present invention.

Also, the substrate 91 in FIG. 8 may be bent by an angle (for example, of 90 to 145 degrees) larger than the right angle as in the fifth embodiment shown in FIG. 9 or smaller than the angle shown in FIG. 8.

A flexible substrate may be used for the substrate 91 in FIG. 9 to have a bending habit so that, even in case the curvable part is curved, no tensile force unfavorable to the respective signal lines 47a may act.

In the second embodiment, the landless through hole is used as a connecting means of the CCD base 52 with the substrate 54. This connecting means can be applied also to the case of connecting the substrate 54 with another substrate.

In the above described embodiments, the imaging surface is arranged so as to be parallel with the lengthwise direction of the insertable part but may be arranged as inclined somewhat or by several tens of degrees from this parallel direction.

As described above, according to the first to fifth embodiments, in the electronic endoscope wherein the solid state imaging device is arranged within the tip so that the imaging surface may be substantially in parallel with the lengthwise direction of the insertable part, as the substrate fitted with the electronic part is connected to the front surface side of the base fitted with the solid state imaging device chip, the tip can be made smaller in the diameter at least by the thickness of this substrate.

In case the driving circuit, preamplifier or coordinating circuit is contained within the tip, when the circuit substrate fitted with the circuit parts is fitted to the base member, it will be easy to incorporate the substrate into the tip and to repair and replace it.

Figure 10:
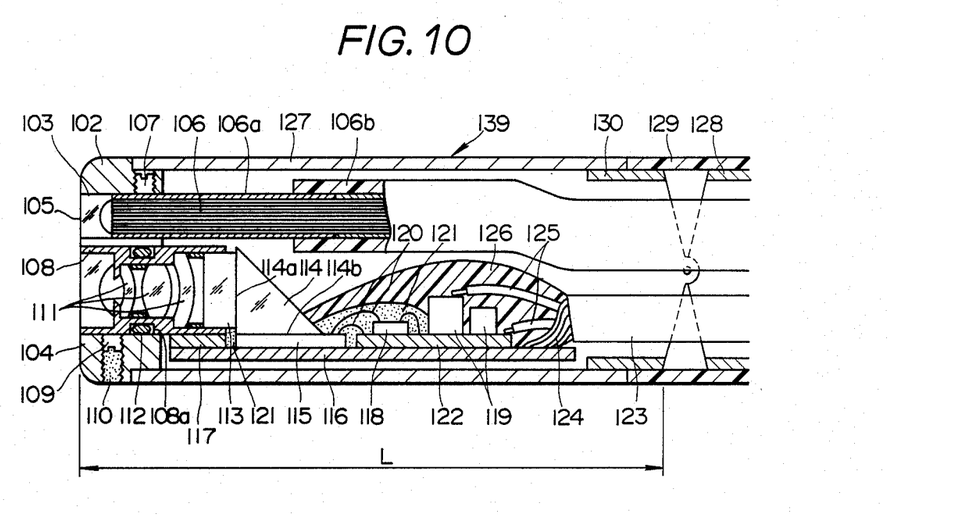
FIG. 10 is a sectioned view of a tip in the seventh embodiment of this invention.

FIG. 10 shows a tip to be an essential part of the sixth embodiment of the present invention.

That is to say, a tip 139 is provided with a substantially columnar tip forming part 102 made of such rigid material as a metal. An illuminating through hole 103 and observing through hole 104 and forceps channel through hole and air and water feeding channel through hole not illustrated all passing in the lengthwise direction through the insertable part are formed in this tip forming part 102. In the illuminating through hole 103, an illuminating lens 105 is fitted from the distal side and then a light guide 106 is fitted to the through hole 103 with a screw 107 from the direction at right angles with the optical axis of the illuminating lens 105. This light guide 106 as coated with a metal pipe 106a on the tip side is coated with a coating member 106b until the intermediate part of a tip 139. In the observing through hole 104, an objective lens frame 108 is fitted and is fixed with a screw 109 from the direction at right angles with the optical axis of the objective lens integrally with a supporting member 116 having also the function of the base member. After is is fixed with the screw 109, the hole for the screw is filled with a filler 110. An objective system 111 is positioned and fitted in this objective lens frame 108. A packing 112 is arranged in a space between the inner wall surface of the observing through hole and a groove 108a formed on the outer wall surface of the lens frame 108. A parallel plane glass plate 113 is fitted and secured on the rear end side of the lens frame 108. A reflecting prism 114 is secured to the rear end surface of this parallel plane glass plate 113 so that the entrance surface 114a may be vertical to the optical axis of the objective lens system 111 and the exit surface 114b may be parallel with the optical axis of the objective lens system 111. A solid state imaging device 115 such as a CCD or SIT is secured to the exit surface 114b of the prism 114. A color filter though not illustrated is provided in a so-called chip-on type on the light entrance surface side of this solid state imaging device 115 which is secured on a plate-like supporting member 116. This supporting member 116 is made, for example, of a metal plate and preferably has a low thermal expansion coefficient so that, when the temperature varies, the supporting member 116 may not peel off the solid state imaging device 115. For example, a 12-chromium stainless steel, 18-chromium stainless steel or moblybdenum steel as plated with nickel or gold is used. Ceramics such as alumina or glass provided with a conductive pattern will also do. This supporting member 116 extends until below the cylindrical lens frame 108. The plate-like supporting member 116 and cylindrical lens frame 108 are secured in close contact with a connecting member 117 made of a metal between them. Therefore, this connecting member 117 is formed to be plane on the side to be secured to the supporting member 116 and to be cylindrical on the side to be secured to the lens frame 108. The space formed of the rear end surface of this connecting member 117, the front end surface of the solid state imaging device 115 and the entrance surface 114a of the prism 114 is filled with a sealing resin 112. Further, on the supporting member 116, a ceramic substrate 122 is secured to the rear side of the solid state imaging device 115. On this ceramic substrate 122, a peripheral IC (integrated circuit) chip 118 is arranged near the solid state imaging device 116 side and electronic parts 119 such as a chip condenser and chip resistance are arranged in the rear of the peripheral IC chip 118. Some of the external electrodes of the solid state imaging device 115 are connected with the substrate 122 and the others of them are connected with the peripheral IC chip 118 through bonding wires 120. This peripheral IC chip 118 and wire bonding parts are resin-sealed with a sealing resin 121. In a cable 123 extending from the operating part side of the endoscope, shielding wires are bundled and are further coated. The external conductors of the respective shielding wires and the outermost shielding wires 124 are soldered to the rear surface side of the supporting member 116. Core wires 125 are connected to the electronic part 119 and substrate 122. The above mentioned sealing resin 121, electronic part 119, shielding wires 124, core wires 125 and substrate 122 are covered with a filler 126 from above. For example, a silicone type bonding agent having an elasticity is used for this filler 126. In a formation as mentioned above, the supporting member 117 and lens frame 108 are kept conductive. The peripheral IC chip 118, substrate 122 and supporting member 116 are also electrically connected. The objective lens frame 108, solid state imaging device 115, supporting member 116, substrate 122 and cable 123 are integrally removable from the tip forming part 102 by removing the screw 109. The tip forming part 102 is fitted and secured at the rear end to the tip of a rigid cylindrical outer tube 127 so as to enclose such contents as the light guides 106 and supporting member 116. This outer tube 127 of the tip is of a length extending further beyond the rear end of the supporting member 116. On the other hand, within a curvable part 140 adjacent to the above mentioned tip 139, many substantially annular articulating frames 128 are rotatably connected in the lengthwise direction and the foremost articulating frame 128 is connected to a curvable tube 130 fitted and secured to the rear end of the above mentioned outer tube 127 of the tip. These articulating frames 128 are coated with a curvable rubber 129 to be an outer skin secured to the rear end of the curvable tube 130.

Figure 11:
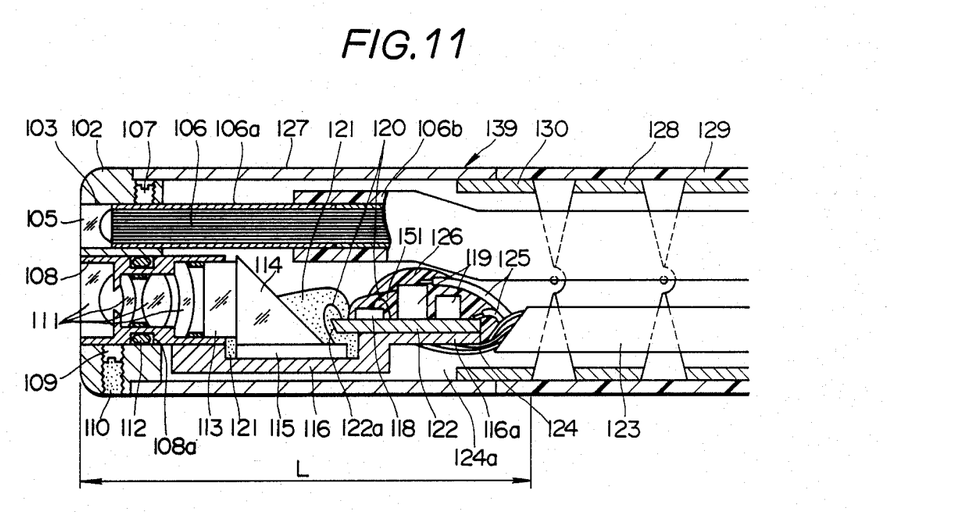
FIG. 11 is a sectioned view of a tip in the eighth embodiment of this invention.

FIG. 11 is a sectioned view of a tip of an endoscope showing the seventh embodiment of this invention. The same functional parts as the parts shown in FIG. 10 are indicated by attaching the same reference numerals. In this embodiment, the connecting member 117 in FIG. 10 is formed integrally with the supporting member 116. The supporting member 116 has a step part 116a formed in the rear of the solid state imaging device 115. In this embodiment, the lower end surface of the step part 116a is located above the lower end surface of the solid state imaging device 115. That is to say, an incision 124a is formed by scraping off the back surface side of the step part 116a. The shielding wires 124 are soldered to the back surface side of the step part 116 which is this incision 124a. By such a connection, the part extending rearward of the substrate 122 of the supporting member 116 can be reduced and the rigid tip length L can be made short. That is to say, the connecting part with the supporting member 116 of the cable 123 is overlapped with the substrate 122 in the inserting axial direction. Without scraping very much, even if the back surface of the step part 116a is scraped off to avoid the fitting part at the rear end of the outer tube 127 of the curvable tube 130, the curvable tube 130 can be overlapped with the supporting member 116 in the axial direction and therefore the rigid tip length L can be made shorter. Also, in this embodiment, the lower end surface of the step part 116a of the supporting member 116 is located above the lower end surface of the solid state imaging device 115 but need not always be. However, when the substrate 122 is overlapped with the solid state imaging device 115 in the inserting axial direction, the rigid tip length L can be made shorter. Further, the distal side end surface 122a of the substrate 122 is formed to be oblique to secure a space for the bonding pads of the bonding wires 120 and to prevent interference with the bonding wires 120.

The substrate 122 as fitted with the peripheral IC chip 18 and electronic part 19 is resin-sealed with a sealing resin 151 and therefore may be taken out of a clean room into a dirty environment. Further, the space between the solid state imaging device 115 and substrate 122 is resin-sealed with the sealing resin 121. The part above the substrate 122 and the part of the core wires 125 of the cable 123 are covered with the filler 126.

Both side surfaces and the upper surfaces of the prism 114, solid state imaging device 115, substrate 122 and electronic part 119 may be shielded with a shielding member.

Due to the formation as mentioned above, the force applied to the cable 123 when curved will be received by one lens frame through the supporting member 116 and therefore, between the solid state imaging device 115 and prism 114 and between the parallel plane glass plate 126 and prism 114, peeling will hardly occur.

Figure 12:
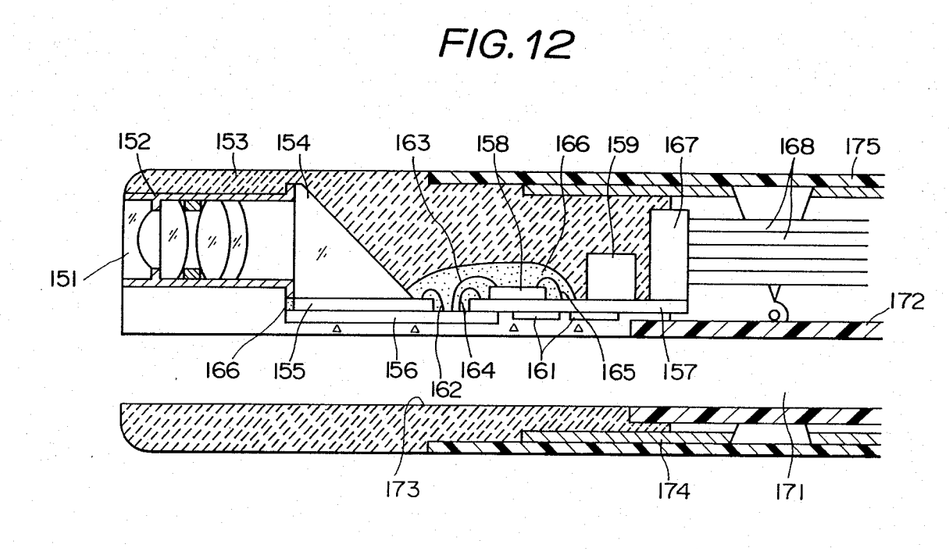
FIG. 12 is a sectioned view of a tip of the ninth embodiment of the present invention.

In the ninth embodiment of the present invention shown in FIG. 12, a lens frame 152 or the like fitted with an objective lens 151 is fixed to a tip forming member 153 molded of a ceramic bonding agent. A prism 154 is fitted on the entrance surface to the rear end of the lens frame 152 and has a solid state imaging device chip 155 secured on the exit surface.

The above mentioned solid state imaging device chip 155 is die-bonded on the back surface to a base member 156 formed of a ceramic substrate, glass epoxy substrate or metal base substrate (in which a circuit pattern is formed on such metal plate as a copper plate). A circuit substrate 157 is fixed at the front end on the upper surface (front surface) near the rear end of this base member 156 and is fitted on the upper surface side with an integrated circuit chip 158 and chip condenser 159. This circuit substrate 157 is fitted on the back surface with printed resistances 161 thinner (not exceeding at least the thickness of the base member 156) than the thickness of the base member 156 so that the tip may not become large in the diameter.

The above mentioned base member 156 is electrically connected with an external electrode of the solid state imaging device chip 155 through a bonding wire 162 and with the circuit substrate 157 and the integrated circuit chip 158 fitted to this circuit substrate 157 respectively through bonding wires 164 and 163. The integrated circuit chip 158 is electrically connected with the circuit substrate 157 through a bonding wire 165. The surface (including the sides) facing the connecting part by the bonding wires 162, 163, 164 and 165 and the outside of the solid state imaging device chip 155 is sealed with a sealing resin 166.

A cable terminal 167 is electrically and mechanically connected to the upper surface of the rear end of the above mentioned circuit substrate 157 and is fitted with signal cables 168 at the ends.

The above mentioned base member 156 and circuit substrate 157 fitted with the printed resistances 161 are covered on the back surfaces with the ceramic bonding agent 153 but a through hole 173 communicating with the opening end of a tube 172 forming a forceps channel 171 is formed as slightly separated from the back surface of this base member 156. In this case, the tube 172 is secured at the tip with the bonding agent forming the tip forming member 153 without making a step on the inner peripheral surface of the through hole 173.

In case the forceps channel 171 is seen in the direction parallel with the optical axis from the left side in FIG. 12, the back surface of the base member 156 will partly overlap with the outer periphery of the tube 172. Thus, the forceps channel 171 is provided toward the upper part (in FIG. 12) to make the tip small in the diameter.

An articulating frame 174 in the foremost step forming a curvable part is secured on the rear end side of the tip forming member. This articulating frame 174 is covered on the outer periphery with an outer cover 175 which is secured at the front end to the tip forming member 153.

Figure 13:
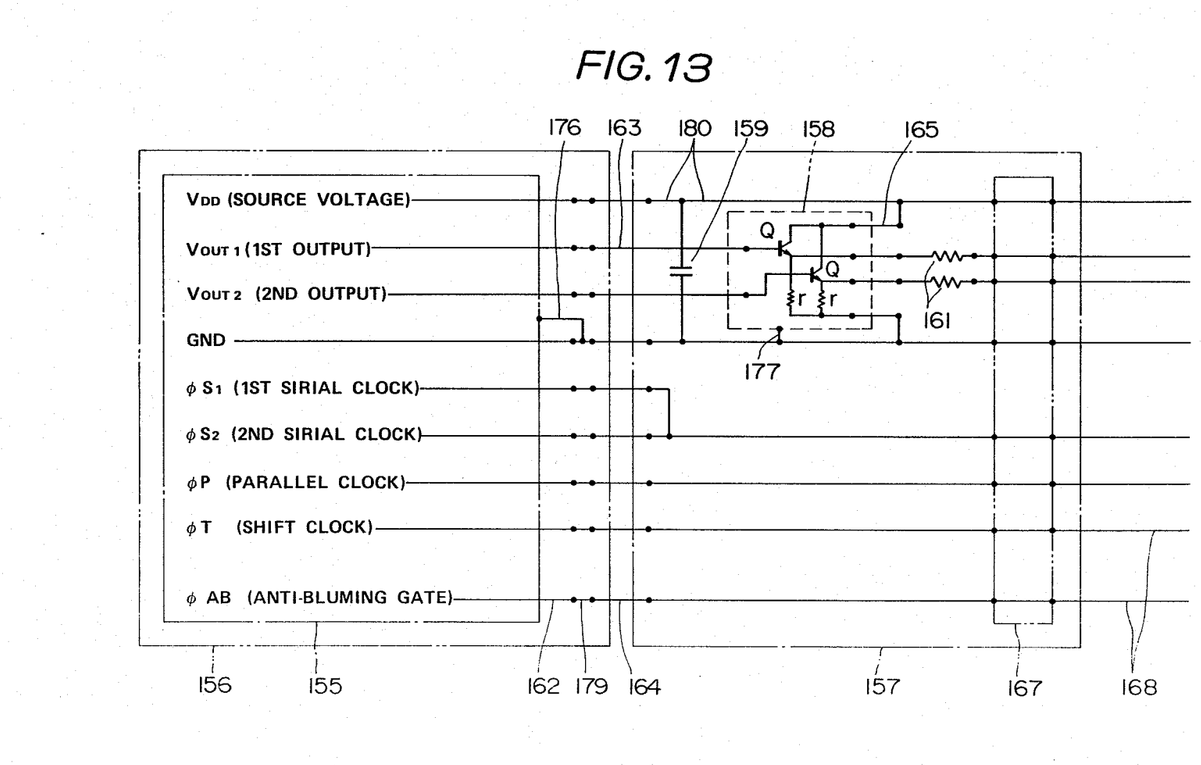
FIG. 13 is a circuit diagram showing peripheral circuits contained within the tip of the ninth embodiment.

Now, the integrated circuit chip 158 or the like fitted to the above mentioned circuit substrate 157 forms the circuit shown in FIG. 13.

The solid state imaging device chip 155 has such external electrodes as $V_{DD}$ for the current source voltage, $V_{out\ 1}$ and $V_{out\ 2}$ for the first and second signal outputs, GND for grounding, $\phi S_1$ and $\phi S_2$ for applying the first and second serial clock pulses, $\phi P$ for applying parallel clock pulses, $\phi T$ for applying shift clock pulses from the first horizontal shift register to the second horizontal shift register and $\phi AB$ for applying anti-blooming gate pulses. $V_{out\ 1}$ and $V_{out\ 2}$ are input into a current amplifier formed of the integrated circuit chip 158. That is to say, $V_{out\ 1}$ and $V_{out\ 2}$ are applied to the bases of a pair of emitter-follower type transistors Q, are current-amplified and are output from the emitters connected to GND respectively through resistances r. The signals output from the respective emitters pass through the printed resistances 161 and are input into a signal processing circuit not illustrated on the proximal side.

The chip condenser 159 is connected to $V_{DD}$ and GND. GND of the solid state imaging device chip 155 connects 176 the chip 155 on the back surface to the base member 156 by die-bonding. The integrated circuit chip 158 is also connected 177 on the back surface to the circuit substrate 157 by die-bonding.

Through the connecting part of the solid state imaging device chip 155 and base member 156 by the bonding wire 162 and the connecting part of the circuit pattern 179 of the base member 156, base member 156 and circuit substrate 157 by the bonding wire 164, the respective external electrodes of the solid state imaging device chip 155 are electrically connected with the circuit substrate 157 side.

For example, the current source voltage terminal $V_{DD}$ is connected with the signal cable 168 through the circuit pattern 180 of the circuit substrate 157.

In FIG. 12 or the like, the base member and circuit substrate or the circuit substrate and IC chip may be connected with each other by face-bonding.

As the electronic part 21 and signal cable 47 in FIG. 1 are arranged within the projected area of the base member 20, CCD chip 19 and prism 18 as seen in the optical axial direction as shown in FIG. 2, the interference with the treating tool channel 26 tube 25, light guide 27 and air and water feeding channel 28 forming tube 18A can be prevented and the tip can be made small in diameter. (The signal cable connecting part 46 and integrated circuit 53 in FIG. 5, the stay 83 and substrate 73 in FIG. 7, the substrate 91 in Figs. 8 and 9, the electronic part 119 and filler 126 in FIG. 10 and the signal cable terminal 167 and printed resistances 161 in FIG. 12 as seen in the optical axial direction are also in the same manner.) In FIG. 2, the substrate 22 is wider than the base 20 but the pattern within the substrate 22 is arranged by using the wider part.

What is claimed is:

1. An electronic endoscope tip comprising:
   an objective optical system contained within a rigid tip in an elongated insertable part and having an optical axis substantially in parallel with an axis of said insertable part;
   an optical device arranged on the optical axis of said objective system and changing an incident light to be in a direction at right angles;
   a solid state imaging device chip having an imaging surface arranged in an exit direction of said optical device and having said imaging surface substantially in parallel with the axis of said insertable part;
   a base member having said solid state imaging device chip fitted to one surface side; and
   a circuit substrate arranged near said solid state imaging device chip and fitted on said one surface side of said base member, said circuit substrate being fitted with an electronic part, and being electrically fitted with a signal transmitting cable at a first end.

2. An electronic endoscope tip according to claim 1 wherein said solid state imaging device chip is die-bonded on a back surface side to said base member.

3. An electronic endoscope tip according to claim 1 wherein said solid state imaging device chip has external electrodes electrically connected with bonding pads in said base member.

4. An electronic endoscope tip according to any one of claims 1, 2 or 3 wherein printed patterns are formed respectively on said one surface side of said base member at an end adjacent said objective optical system and on a second end of said circuit substrate, and said circuit substrate is mechanically fixed and electrically connected to said base member at soldering parts in said printed patterns.

5. An electronic endoscope tip according to any one of claims 1, 2 or 3 wherein said base member and circuit substrate are connected with each other by wire-bonding.

6. An electronic endoscope tip according to any of claims 1, 2 or 3 wherein through holes are formed respectively at the end adjacent said objective optical system in said base member and at said second end of said circuit substrate, said circuit substrate is arranged on said one surface side and a metal bar is inserted at respective ends into both said through holes and is soldered to mechanically fix and electrically connect said circuit substrate to said base member.

7. An electronic endoscope tip according to claim 6 wherein said circuit substrate is fitted in close contact with said one surface of said base member.

8. An electronic endoscope tip according to claim 6 wherein said metal bar is fitted in small diameter parts at both ends into said respective through holes and is soldered to mechanically fix and electrically connect said circuit substrate to said base member.

9. An electronic endoscope tip according to any one of claims 1, 2 or 3 wherein each of said through hole is a landless through hole.

10. An electronic endoscope tip according to any of claims 1, 2 or 3 wherein said circuit substrate is bent near a part fitted to said base member so that a back surface opposed to said one surface side of said base member faces toward a rear end side of said rigid tip.

11. An electronic endoscope tip according to claim 10 wherein the bending angle of said bend is 90 degrees.

12. An electronic endoscope tip according to claim 10 wherein the bending angle of said bend is 90 to 145 degrees.

13. An electronic endoscope tip according to any one of claims 1, 2 or 3 wherein said signal cable is electrically connected by soldering to respective through holes formed on a bent end side of said circuit substrate and on an opposite end side.

14. An electronic endoscope tip according to claim 1 wherein said base member is any of a ceramic printed substrate, glass epoxy substrate and metal base printed substrate.

15. An electronic endoscope tip according to claim 1 wherein said base member is formed of a metal plate.

16. An electronic endoscope tip according to claim 15 wherein said base member has a solid state imaging device chip which is die-bonded thereto.

17. An electronic endoscope tip according to claim 15 wherein shielding wires of a signal cable are connected to said base member.

18. An electronic endoscope tip according to claim 15 wherein the metal plate forming said base member is of a stainless steel which is plated.

19. An electronic endoscope tip according to any one of claims 1, 15 or 18 wherein a part of said base member is fitted with said solid state imaging device chip, said base member having a step surface projecting from a rear end side adjacent to said objective optical system in a direction vertical to said one surface, and said circuit substrate is fitted to said step surface.

20. An electronic endoscope tip according to claim 19 wherein an incision is made on the back surface side of the step surface fitted with said circuit substrate and said signal transmitting cable is fitted at the end to said incision.

21. An electronic endoscope tip according to any one of claims 15-18 wherein said circuit substrate is fitted with an integrated circuit chip together with an electronic part.

22. An electronic endoscope tip according to claim 21 wherein the external electrodes of said solid state imaging device chip are electrically connected with said integrated circuit chip by bonding wires.

23. An electronic endoscope tip according to any one of claims 15-18 wherein the external electrodes of said solid state imaging device chip are electrically connected with said circuit substrate by bonding wires.

24. An electronic endoscope tip according to any one of claims 15-18 wherein said circuit substrate fitted to said base member and fitted with the electronic part is covered on the periphery with a filler.

25. An electronic endoscope tip according to any one of claims 15-18 wherein said base member is secured at a front end to a lens frame fitted with said objective optical system.

26. An electronic endoscope tip according to claim 1 wherein said electronic part and electronic part connecting terminals are provided within a projected area of all of said optical device, solid state imaging device chip and base member as seen in the optical axial direction.

27. An electronic endoscope tip according to claim 1 wherein said signal transmitting cable is connected substantially at right angles with a through hole of said circuit substrate and a height of the signal transmitting cable connecting part projecting on a back surface of said circuit substrate does not exceed a thickness of said base member.

28. An electronic endoscope tip according to claim 1 wherein said circuit substrate is provided on a back surface with an electronic part of a height not exceeding the thickness of said base member.

29. An electronic endoscope tip according to claim 28 wherein said electronic part is a printed resistance.

30. An electronic endoscope tip according to claim 1 wherein a component member, forming the tip of the electronic endoscope, is provided as at least partly overlapped within a projected area of said base member as seen in the optical axial direction.

31. An electronic endoscope tip according to claim 30 wherein said component member is an articulating frame.

32. An electronic endoscope tip according to claim 30 wherein said component member is a forceps channel tube.

33. An electronic endoscope tip comprising:
an objective optical system contained within a rigid tip in an elongated insertable part and having an optical axis substantially in parallel with an axis of said insertable part;
an optical device arranged on the optical axis of said objective system and changing an incident light to be in a direction at right angles;
a solid state imaging device chip having an imaging surface arranged in an exit direction of said optical device and having said imaging surface substantially in parallel with the axis of said insertable part;
a base member having said solid state imaging device chip fitted to one surface side; and
a circuit substrate arranged near said solid state imaging device chip and fitted on said one surface side of said base member, said circuit substrate being fitted with an electronic part, and being electrically fitted with a signal transmitting cable at a first end, wherein said solid state imaging device chip and said circuit substrate are electrically connected on said one surface side and wherein said base member and said circuit substrate are electrically connected on said one surface side at an end of said base member opposite said solid state imaging device chip.

* * * * *